United States Patent
Fujii et al.

(10) Patent No.: US 8,609,138 B2
(45) Date of Patent: Dec. 17, 2013

(54) ω3 FATTY ACID COMPOUND PREPARATION

(75) Inventors: Hirosato Fujii, Shizuoka (JP); Hiromitsu Ito, Shizuoka (JP); Motoo Yamagata, Shizuoka (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/806,032

(22) PCT Filed: Jun. 29, 2011

(86) PCT No.: PCT/JP2011/064976

§ 371 (c)(1),
(2), (4) Date: Dec. 20, 2012

(87) PCT Pub. No.: WO2012/002464

PCT Pub. Date: Jan. 5, 2012

(65) Prior Publication Data

US 2013/0115284 A1      May 9, 2013

(30) Foreign Application Priority Data

Jun. 30, 2010   (JP) ................................ 2010-150611

(51) Int. Cl.
*A61K 9/48*      (2006.01)
*A61K 31/22*     (2006.01)
*A61K 31/505*    (2006.01)
*A61K 31/557*    (2006.01)

(52) U.S. Cl.
USPC ............ 424/456; 424/463; 514/547; 514/275

(58) Field of Classification Search
None
See application file for complete search history.

(56) References Cited

U.S. PATENT DOCUMENTS

| | | | |
|---|---|---|---|
| 5,030,447 A * | 7/1991 | Joshi et al. ................. | 514/510 |
| 5,356,896 A | 10/1994 | Kabadi et al. | |
| 5,641,512 A | 6/1997 | Cimiluca | |
| 2009/0196920 A1 | 8/2009 | Carminati et al. | |
| 2010/0068265 A1 | 3/2010 | Ottinger et al. | |
| 2010/0285121 A1 * | 11/2010 | Uchiyama et al. ............ | 424/463 |

FOREIGN PATENT DOCUMENTS

| | | | |
|---|---|---|---|
| JP | 55-138457 A | | 10/1980 |
| JP | 2-6406 A | | 1/1990 |
| JP | 3-8435 A | | 1/1991 |
| JP | 5-246844 A | | 9/1993 |
| JP | 11-502838 A | | 3/1999 |
| JP | 2003-2829 A | | 1/2003 |
| JP | 2003-73270 A | | 3/2003 |
| JP | 2004-2473 A | | 1/2004 |
| JP | 2004-196706 A | | 7/2004 |
| JP | 3719679 B2 | | 11/2005 |
| JP | 2010-513351 A | | 4/2010 |
| JP | 2010-260812 A | | 11/2010 |
| WO | WO 2006/045865 A1 | | 5/2006 |
| WO | WO 2006/096806 A2 | | 9/2006 |
| WO | WO 2007/103557 A2 | | 9/2007 |
| WO | WO-2007-130714 | * | 11/2007 |
| WO | WO 2007/130714 A1 | | 11/2007 |
| WO | WO 2009/087938 A1 | | 7/2009 |

OTHER PUBLICATIONS

International Search Report, dated Aug. 20, 2011, for International Application No. PCT/JP2011/064976.
Miida et al., "Prevention of stroke and dementia by strain therapy: Experimental and clinical evidence of their pleiotropic effects", Pharmacology & Therapeutics, vol. 113, 2007, pp. 378-393.
Yokoyama et al., "Effects of eicosapentaenoic acid on major coronary events in hypercholesterolaemic patients (JELIS): a randomised open-label, blinded endpoint analysis", Lancet, vol. 369, Mar. 31, 2007, pp. 1090-1098.
International Preliminary Report on Patentability and Translation of the Written Opinion of the International Searching Authority, dated Feb. 21, 2013, for International Application No. PCT/JP2011/064976 (Forms PCT/IB/338, PCT/IB/373 and PCT/ISA/237).

* cited by examiner

*Primary Examiner* — Frederick Krass
*Assistant Examiner* — Celeste A Roney
(74) *Attorney, Agent, or Firm* — Birch, Stewart, Kolasch & Birch, LLP

(57) ABSTRACT

Provided is a compound preparation including at least one selected from the group consisting of ω3 polyunsaturated fatty acids and pharmaceutically acceptable salts and esters thereof and at least one selected from the group consisting of statin compounds and pharmaceutically acceptable salts thereof. The compound preparation is in a form of a soft capsule having a capsule coating with a pH of 7.0 to 9.5. The compound preparation suppresses the decomposition of the statin compounds and/or the modification/insolubilization of the capsule coating. A medical use for the compound preparation, a method of manufacturing the compound preparation and a method of using the compound preparation are also provided.

9 Claims, No Drawings

ω3 FATTY ACID COMPOUND PREPARATION

TECHNICAL FIELD

The present invention provides a soft capsule which comprises at least one selected from the group consisting of ω3 polyunsaturated fatty acids and pharmaceutically acceptable salts and esters thereof, and at least one selected from the group consisting of statin compounds, and a compound preparation and a manufacturing method thereof.

BACKGROUND ART

Westernization of diet has resulted in an increase of patients suffering from lifestyle-related diseases such as hyperlipidemia, diabetes, and hypertension. Some of these diseases finally lead to arteriosclerotic diseases such as myocardial infarction, angina pectoris, and cerebral infarction. It is important to reduce risk factors such as hyperlipidemia, diabetes, hypertension and smoking habit as much as possible in order to prevent arteriosclerotic diseases or improve the quality of life. As a result of a main epidemiological study made on the incidence of hyperlipidemia and coronary artery diseases, the serum total cholesterol (hereinafter abbreviated as "T-Cho") concentration or the serum triglyceride (hereinafter abbreviated as "TG") concentration shows a positive correlation with the onset of the coronary artery diseases. In particular, the serum low-density lipoprotein cholesterol (hereinafter abbreviated as "LDL-Cho") concentration shows a much stronger positive correlation therewith. On the other hand, the serum high-density lipoprotein cholesterol (hereinafter abbreviated as "HDL-Cho") concentration shows a negative correlation therewith.

Omega-3 polyunsaturated fatty acids (hereinafter abbreviated as "ω3PUFAs") including α-linolenic acid, icosapentaenoic acid (hereinafter referred to as "EPA"), and docosahexaenoic acid (hereinafter referred to as "DHA") are known. Omega-3PUFAs and their pharmaceutically acceptable salts and esters (hereinafter referred to as "ω3PUFA salts/esters") exhibit various actions including anti-arteriosclerotic action, platelet aggregation inhibitory action, hypolipidemic action, anti-inflammatory action, antitumor action and central action, and are therefore incorporated in various food products or commercially available as health food products or pharmaceutical products.

A high purity EPA ethyl ester (hereinafter referred to as "EPA-E") is commercially available in Japan in the trade names of Epadel and Epadel S (manufactured by Mochida Pharmaceutical Co., Ltd.) as drugs for alleviating ulcers, pain and chill associated with arteriosclerosis obliterans and for treating hyperlipidemia. Soft capsules containing about 46 wt % of EPA-E and about 38 wt % of DNA ethyl ester (hereinafter referred to as "DHA-E") are commercially available in the U.S., Europe, and other countries in the trade names of Omacor and Lovaza as therapeutic agents for hypertriglyceridemia.

A statin compound (hereinafter also referred to as statin) is a generic name used to refer to a drug for lowering cholesterol levels in blood by inhibiting the action of HMG-CoA reductase. The result that the onset of coronary artery diseases was suppressed by the use of statin compounds in the therapy for hyperlipidemia is obtained in a large-scale clinical trial.

Six statins are currently available in Japan as pharmaceutical products. Based on the physicochemical properties (log $P_{7.4}$; water-octanol partition coefficient at a pH of 7.4), these statins are classified into two groups including water-soluble statins (pravastatin (−0.84), rosuvastatin (~0.33)) and fat-soluble statins (atorvastatin (1.11), simvastatin (1.60) and the like). (Non-Patent Literature 1) Pravastatin sodium, rosuvastatin calcium and atorvastatin calcium which are the corresponding pharmaceutical products have partition coefficients (octanol-water partition coefficient) of −0.33 (Non-Patent Literature 2), −0.3±0.1 (Non-Patent Literature 3) and 1.21 (Non-Patent Literature 4), respectively.

In recent years, a single pharmaceutical preparation (compound preparation) containing a plurality of pharmaceutically active ingredients is under active development in the pharmaceutical field in order to improve, for example, the pharmacodynamic synergism, the reduction of side effects, the convenience for patients and the compliance.

A large-scale randomized controlled clinical trial PELTS trial) was conducted to know the effect of Epadel on the suppression of the onset of ischemic heart diseases in patients administered with a statin for the treatment of hyperlipidemia, and its main analysis shows the evidence that the incidence of major coronary events is significantly low in the group administered with Epadel in combination according to the comparison between the administered group and the non-administered group. (Non-Patent Literature 5) When attention is focused on the treatment of lifestyle-related diseases, it is deemed significant for the medication to take notice of the clinical effects of the ω3PUFAs and the statins and to develop compound preparations containing both the drugs.

Various reports have been made on preparations (compound preparations) each containing two pharmaceutically active ingredients in which an ω3PUFA alkyl ester and a statin which are liquid at room temperature are encapsulated. However, several problems are to be solved to supply stable preparations over the manufacture, distribution and storage periods, and these preparations are not yet in practical use.

Statin compounds such as pravastatin sodium and atorvastatin calcium hydrate are HMG-CoA reductase inhibitors and are used as excellent oral drugs for treating hyperlipidemia or hypercholesterolemia. However, it is already known that such statin compounds have a 7-substituted-3,5-dihydroxy-6-heptenoic acid structure and are unstable with respect to high temperature, high humidity and light because of the molecular structure and are excessively destabilized due to the intramolecular lactonization, isomerization, oxidation, decomposition or the like in the acidic region and that stable preparations cannot be obtained unless at least the pH is more than 7. Preparation using alkaline excipients at a pH of more than 9 such as calcium carbonate, anhydrous disodium phosphate, sodium hydroxide, potassium hydroxide and magnesium oxide (Patent Literatures 1, 2, 3) and preparation using magnesium metasilicate aluminate at a pH of more than 9 as the stabilizer (Patent Literatures 4, 5, 6) have been reported in order to solve this problem. However, there is no application to soft capsules or to drugs combined with ω3PUFA salts/esters and the applicability is uncertain.

The main ingredient of gelatin widely used in capsules is protein. Protein is known to have the property of being easily modified by the application of physical factors (e.g., heating, freezing, vigorous agitation) and chemical factors (e.g., addition of acids, bases, organic chemicals and heavy metal ions), thus losing the water solubility to be insolubilized. In fact, when gelatin is used in the capsule coating, it is known that the solubility of the coating generally tends to be reduced over time by crosslinking caused by the interaction of gelatin molecules with an encapsulated material or the material after decomposition. That is, the gelatin capsule coating may be modified depending on the formulation condition and there is concern that the function as the pharmaceutical composition may be lost.

A soft gelatin capsule obtained by suspending a microcapsule comprising at least one polymer and a statin in an ω3PUFA alkyl ester has been reported. (Patent Literature 7) Even when the manufacturing process is performed at a temperature of 40° C., the statin can be prevented from being decomposed by incorporating the statin in the microcapsule upon compounding of the statin in a pharmaceutically active liquid ingredient containing the ω3PUFA alkyl ester in a large amount. However, the amount of statin to be incorporated is limited because the stability during the distribution and storage after the manufacture is uncertain, the microcapsule amount is 1 to 60% of the total amount of the preparation and the statin content in the microcapsule is 1 to 40% of the total amount of the microcapsule. In addition, this technique is only applied to fat-soluble statins and it is not certain whether it can be applied to water-soluble statins.

A capsule prepared by combining at least one ω3PUFA salt/ester, at least one statin, and optionally at least one hydrophilic solvent and/or at least one surfactant and/or other solubilizer and/or other excipient has been reported (Patent Literature 8). However, it would be difficult to control the content of the statin ingredient within a predetermined allowable range during the manufacture because the stability of the capsule is not mentioned and is hence uncertain, there is concern about side effects due to a high surfactant content and the statin is not completely dissolved in the ω3PUFA. In addition, this technique is only applied to fat-soluble statins and it is not certain whether it can be applied to water-soluble statins.

A pharmaceutical composition comprising a hard or soft capsule containing a ω3PUFA salt/ester as a first active pharmaceutical ingredient, a carrier and optionally a solubilizer and a coating of a statin serving as a second active pharmaceutical ingredient formed on the hard or soft capsule has been reported (Patent Literature 9). However, the pharmaceutical composition will have difficulty in controlling the content of the statin ingredient within a predetermined allowable range and suffer from a complicated step and a low yield when the coating is formed, A seamless capsule comprising an ω3PUFA alkyl ester encapsulated in the form of a liquid pharmaceutical composition, wherein (1) a statin serving as a solid pharmaceutically active ingredient is dispersed in a capsule shell layer, (2) the statin is dispersed in the liquid pharmaceutical composition or (3) the statin is applied onto the capsule shell layer having no pharmaceutically active ingredient has been reported (Patent Literature 10). However, since the stability is not mentioned and is uncertain in the shapes of (1) and (3) and the solid ingredient is present in the capsule coating in the shape of (1), there is concern about the stability of the seamless capsule and it is deemed to be difficult to increase the amount of the solid pharmaceutically active ingredient; and in the shapes of (2) and (3), the pharmaceutical composition will have difficulty in controlling the content of the statin ingredient as described above within a predetermined allowable range and suffer from a low yield. In addition, this technique is only applied to fat-soluble statins and it is not certain whether it can be applied to water-soluble statins.

CITATION LIST

Non-Patent Literature

Non-Patent Literature 1: Pharmacology & Therapeutics, vol. 113, pp. 378-393 (2007)

Non-Patent Literature 2: Drug Interview Form "Mevalotin", revised in July 2010, 7th edition, Daiichi Sankyo Co., Ltd.

Non-Patent Literature 3: Drug Interview Form "Crestor", revised in January, 2011, 10th edition, AstraZeneca K.K., Shionogi & Co., Ltd.

Non-patent Literature 4: Drug Interview Form "Lipitor", revised in June 2010, 18th edition, Astellas Pharma Inc., Pfizer Inc.

Non-Patent Literature 5: Lancet, vol. 369, pp. 1090-1098 (2007)

PATENT LITERATURE

Patent Literature 1: JP 05-246844 A;
Patent Literature 2: JP 02-006406 A;
Patent Literature 3: JP 2003-073270 A;
Patent Literature 4: JP 2003-2829 A;
Patent Literature 5: JP 2004-002473 A;
Patent Literature 6: JP 3719679 B;
Patent Literature 7: WO 2006/045865 (JP 2008-517040 A);
Patent Literature 8: WO 2006/096806 (JP 2008-533029 A)
Patent Literature 9: WO 2007/103557 (JP 2009-529531 A)
Patent Literature 10: WO 2009/087938

SUMMARY OF INVENTION

Technical Problems

The present invention provides a soft capsule containing an ω3PUFA salt/ester and a statin compound and a compound preparation in the form of the soft capsule. The invention more particularly provides a stable soft capsule capable of suppressing the decomposition of the statin compound and/or the modification/insolubilization of the capsule coating over the manufacture period, distribution period and storage period, a compound preparation in the form of the soft capsule as well as a method of manufacturing the same and a method of using the same.

Solution to Problems

The inventors of the present invention have made an intensive study and as a result found that the above-described problems can be solved as described below. The present invention has been thus completed. There arose a need to prevent a statin compound from being decomposed when a ω3PUFA salt/ester is combined with the statin compound (in particular a water-soluble statin compound such as pravastatin or rosuvastatin) in the form of a soft capsule and particularly a gelatin seamless capsule. Then, it was found that the decomposition of the statin compound is suppressed by adjusting the pH of the gelatin coating to a slightly alkaline level and that the stability and particularly the storage stability of the statin compound is dramatically improved by particularly using a carbonate as the buffer. It was also found that incorporation of a carbonate and/or a metasilicate aluminate and/or a phosphate in the gelatin coating increases the storage stability of the statin compound. It was also found that the modification/insolubilization of the gelatin coating can be suppressed while keeping the stability of the statin compound by adding at least one selected from the group consisting of succinylated gelatin, an organic acid, particularly tartaric acid, hydrolyzed gelatin and trehalose to the gelatin coating. It was further found that the modification/insolubilization of the gelatin coating can be likewise suppressed while keeping the stability of the statin compound by applying a water-soluble polymer, particularly hydroxypropyl methylcellulose (hereinafter abbreviated as "HPMC") to the inner surface of the capsule coating. Embodiments of the present invention are described below.

1. A soft capsule comprising at least one selected from ω3PUFA salts/esters and at least one selected from statin compounds, wherein a capsule coating has a pH adjusted to 7.0 to 9.5.
2. The soft capsule according to 1, wherein the at least one selected from the ω3PUFA salts/esters is contained in a capsule content and the at least one selected from the statin compounds is contained in the capsule coating.
3. The soft capsule according to 1 or 2, wherein the capsule coating contains at least one selected from the group consisting of a carbonate, a metasilicate aluminate and a phosphate.
4. The soft capsule according to any one of 1 to 3, wherein the capsule coating contains a carbonate and/or a metasilicate aluminate.
5. The soft capsule according to any one of 1 to 4, wherein the capsule coating contains sodium hydrogen carbonate and/or magnesium metasilicate aluminate.
6. The soft capsule according to any one of 1 to 3, wherein the capsule coating contains gelatin.
7. The soft capsule according to any one of 1 to 6, wherein the capsule coating contains at least one selected from the group consisting of succinylated gelatin, an organic acid, hydrolyzed gelatin and trehalose.
8. The soft capsule according to 7, wherein the organic acid is tartaric acid.
9. The soft capsule according to any one of 1 to 8, wherein a film of a water-soluble polymer is formed on an inner surface of the capsule coating.
10. The soft capsule according to 9, wherein the water-soluble polymer is HPMC.
11. The soft capsule according to any one of 1 to 10, wherein the statin compounds are water-soluble statin compounds.
12. The soft capsule according to any one of 1 to 11, wherein the statin compounds comprise at least one selected from the group consisting of pravastatin and rosuvastatin, and salts and hydrates thereof.
13. The soft capsule according to any one of 1 to 12, wherein the statin compounds comprise pravastatin sodium and/or rosuvastatin calcium.
14. The soft capsule according to any one of 1 to 12, wherein the ω3PUFA salts/esters comprise at least one selected from EPA and DHA and salts and esters thereof.
15. The soft capsule according to any one of 1 to 14, wherein the ω3PUFA salts/esters comprise EPA-E and/or DHA-E.
16. The compound preparation which is in a form of the soft capsule according to any one of 1 to 15.
17. A method of manufacturing a soft capsule comprising at least one selected from ω3PUFA salts/esters and one or more statin compounds or a compound preparation in a form of the soft capsule, the method comprising:
 1) a step of adjusting a capsule coating solution to a pH of 7.0 to 9.5;
 2) a step of dissolving the statin compounds in the capsule coating solution;
 3) a step of preparing a capsule content containing the ω3PUFA salts/esters; and
 4) a step of obtaining the soft capsule from the capsule content and the capsule coating solution.
18. The method according to 17, further comprising a step of adding a carbonate and/or a metasilicate aluminate to the capsule coating solution.
19. The method according to 17 to 18, further comprising a step of adding sodium hydrogen carbonate and/or magnesium metasilicate aluminate to the capsule coating solution.
20. The method according to any one of 17 to 19, further comprising a step of adding gelatin to the capsule coating solution.
21. The method according to any one of 17 to 20, further comprising:
 a step of adding at least one selected from the group consisting of succinylated gelatin, an organic acid, hydrolyzed gelatin and trehalose to the capsule coating solution.
22. The method according to any one of 17 to 21, wherein the organic acid is tartaric acid.
23. The method according to any one of 17 to 22, further comprising:
 1) a step of adding a water-soluble polymer to the ω3PUFA salts/esters (capsule content); and/or
 2) a step of forming a film of the water-soluble polymer on an inner surface of the capsule coating,
24. The method according to 23, wherein the water-soluble polymer is HPMC.
25. The method according to any one of 17 to 24, wherein the statin compounds are water-soluble statin compounds.
26. The method according to any one of 17 to 25, wherein the statin compounds comprise at least one selected from the group consisting of pravastatin and rosuvastatin, and salts and hydrates thereof.
27. The method according to any one of 17 to 26, wherein the statin compounds comprise pravastatin sodium and/or rosuvastatin calcium.
28. The method according to any one of 17 to 27, wherein the ω3PUFA salts/esters comprise at least one selected from EPA and DHA and salts and esters thereof.
29. The method according to any one of 17 to 28, wherein the ω3PUFA salts/esters comprise EPA-E and/or DHA-E.

Advantageous Effects of Invention

The present invention can stabilize the statin compounds and particularly water-soluble statin compounds and/or suppress the modification or insolubilization of the capsule coating and particularly gelatin coating during the manufacture, distribution and/or storage of the soft capsule containing the ω3PUFA salt/ester and statin compound, and the compound preparation in the form of the soft capsule.

Therefore, the soft capsule and the compound preparation according to the present invention have such advantages as good stability during the manufacture, suitability to long-term storage and good bioavailability of the combined ingredients exhibited by the suppressed modification or insolubilization of the capsule coating and particularly gelatin coating. In addition, the method of manufacturing the soft capsule and the compound preparation according to the present invention has such advantages as reduced number of manufacturing steps, easy manufacture, suitable adjustment of the amounts of combined ingredients and good yield.

The compound preparation of the present invention may be used as a prophylactic or therapeutic agent for hyperlipidemia or other diseases.

DESCRIPTION OF EMBODIMENTS

The present invention is described below in detail.

In the present invention, ω3PUFAs are fatty acids, each of which contains a plurality of carbon-carbon double bonds in the molecule and has the first double bond at the third position from the methyl group side. Typical examples thereof include a-linolenic acid, EPA, DHA, eicosatrienoic acid, stearidonic acid, eicosatetraenoic acid, clupanodonic acid, tetracosapentaenoic acid and Nisinic acid. Unless otherwise specified, the term "ω3PUFA salts/esters" as used in the present invention includes not only the ω3PUFAs but also pharmaceutically acceptable salts and esters thereof.

The ω3PUFA salts/esters used in the present invention may be synthetic, semisynthetic or natural products, or be in the form of natural oil containing such polyunsaturated fatty acids. The natural products may be those extracted from natural oil containing the ω3PUFAs salts/esters by a known method or those which have been further processed to produce crude products or further purified products. The semisynthetic products include ω3PUFA salts/esters produced by microorganisms, and also include those obtained by subjecting these ω3PUFA salts/esters or natural ω3PUFA salts/esters to chemical treatments such as esterification and ester exchange. In the present invention, the ω3PUFA salts/esters may be used singly or in combination of two or more thereof.

Exemplary ω3PUFA salts/esters that may be preferably used in the present invention include EPA and/or DHA and EPA is more preferable. Examples of the pharmaceutically acceptable salts of the ω3PUFAs include inorganic bases such as sodium salts and potassium salts; organic bases such as benzylamine salts and diethylamine salts; and basic amino acid salts such as arginine salts and lysine salts. Examples of the pharmaceutically acceptable esters thereof include alkyl esters such as ethyl esters; and mono-, di- and triglyceride esters. Ethyl esters and triglyceride esters are preferable and ethyl esters are more preferable. In other words, EPA-E, EPA triglyceride ester, DHA-E and DHA triglyceride ester are preferable, EPA-E and DHA-E are more preferable, and EPA-E are even more preferable.

The purity of the ω3PUFA salts/esters is not particularly limited, and in general the content of the ω3PUFA salts/esters in the total fatty acids of the capsule content is preferably at least 25 wt %, more preferably at least 45 wt %, even more preferably at least 70 wt %, still even more preferably at least 85 wt % and most preferably at least 96.5 wt %. The purity of EPA-E+DHA-E is preferably high. For example, the content of EPA-E+DHA-E in the ω3PUFA salts/esters is preferably at least 50 wt %, more preferably at least 60 wt %, even more preferably at least 90 wt % and most preferably at least 99 wt %. In other words, the purity of the ω3PUFA salts/esters in the total fatty acids of the capsule content is preferably high, the purity of EPA+DHA which are the ω3PUFA salts/esters is more preferably high, and the purity of EPA is even more preferably high.

For example in the case of using EPA-E and DHA-E, the compositional ratio of EPA-E to DHA-E and the content ratio of EPA-E and DHA-E to the total fatty acids are not particularly limited if the purity of EPA in the composition of the preparation is within the above-defined range. The compositional ratio of EPA-E to DHA-E(EPA-E/DHA-E) is preferably at least 0.8, more preferably at least 1.0 and even more preferably at least 1.2.

The composition of the preparation may contain polyunsaturated fatty acids other than the ω3PUFA salts/esters (e.g., linoleic acid, γ-linolenic acid and dihomo-γ-linolenic acid) and pharmaceutically acceptable salts or esters thereof but arachidonic acid is desirably contained in a small amount, preferably in an amount of less than 2 wt % and more preferably less than 1 wt %. An embodiment in which arachidonic acid is substantially not contained is particularly preferred.

The content of the ω3PUFA salts/esters in the compound preparation of the present invention is not particularly limited and is usually at least 50 wt %, preferably at least 80 wt %, more preferably at least 85 wt % and even more preferably at least 90 wt % of the capsule content.

Compared to fish oil and fish oil concentrates, the ω3PUFA salts/esters used in the present invention contain less impurities such as saturated fatty acids and arachidonic acid which are not preferred to prevent cardiovascular events, and can exhibit their effects without causing any problem of overnutrition or excessive intake of vitamin A. The ω3PUFA salts/esters in ester form have higher oxidation stability than fish oil which is mainly in triglyceride form and a sufficiently stable composition can be obtained by adding a commonly used antioxidant.

The ω3PUFA salt/ester that may be used is a soft capsule containing EPA-E at a high purity (at least 96.5 wt %) (trade name, Epadel; manufactured by Mochida Pharmaceutical Co., Ltd.) which is available in Japan as a therapeutic agent for hyperlipidemia. For example, Lovaza which is a mixture of EPA-E and DHA-E and is commercially available in the U.S. as a therapeutic agent for hypertriglyceridemia may also be used.

The ω3PUFA salt/ester used may also be purified fish oil. Monoglyceride, diglyceride, and triglyceride derivatives of the ω3PUFA salts/esters or combinations thereof constitute preferable embodiments. Various products containing the ω3PUFA salts/esters are commercially available, as exemplified by Incromega F2250, F2628, E2251, F2573, TG2162, TG2779, TG2928, TG3525, and E5015 (Croda International PLC, Yorkshire, England), and EPAX6000FA, EPAX5000TG, EPAX4510TG, EPAX2050TG, EPAX7010EE, K85TG, K8SEE, and K80EE (Pzonova Biopharma, Lysaker, Norway). These products may be purchased and used.

The "statin compounds" as used in the present invention refer to HMG-CoA reductase inhibitors and, unless otherwise specified, include not only statin compounds themselves but also pharmaceutically acceptable salts thereof (e.g., sodium salts and calcium salts) and hydrates thereof. Exemplary statin compounds include cerivastatin, pravastatin, simvastatin, lovastatin, atorvastatin, fluvastatin, rosuvastatin and pitavastatin, and salts and hydrates thereof, such as pravastatin sodium, cerivastatin sodium, atorvastatin calcium hydrate, fluvastatin sodium, rosuvastatin calcium, and pitavastatin calcium. Of those statin compounds described above, the "water-soluble statin compounds" as used in the present invention are pravastatin, rosuvastatin and their corresponding salts and in particular pravastatin sodium and rosuvastatin calcium.

The statin compound used is preferably a water-soluble compound and more specifically pravastatin sodium or rosuvastatin calcium.

In the present invention, the statins are incorporated in any form. For example, a statin may be dissolved or dispersed in a capsule content containing an ω3PUFA salt/ester or applied to a capsule coating by a known suitable method, or dissolved or dispersed in a capsule coating. In a preferred form, however, a statin is incorporated in a capsule coating by dissolving it in a capsule coating liquid and encapsulating it by a known suitable method.

The statin content in the compound preparation of the present invention is not particularly limited and is usually from 0.01 wt % to 20 wt %, preferably from 0.01 wt % to 10 wt % and more preferably from 0.01 wt % to 5 wt % of the compound preparation.

In the present invention, the compounding ratio of ω3PUFA salt/ester to statin is usually 6000:1 to 3:1 and preferably 2000:1 to 10:1 but may be appropriately adjusted depending on, for example, the types of the ω3PUFA salt/ ester and statin used, type of disease, severity of symptoms, body weight and age of a patient to be administered therewith. For example, the compounding ratio is usually 270:1 to 20:1 and preferably 180:1 to 40:1 in the case of incorporating PA-E and/or DHA-E and pravastatin sodium, and is usually 1000:1 to 40:1 and preferably 720:1 to 80:1 in the case of rosuvastatin calcium.

In the present invention, the capsule form is not necessarily limited and a rotary soft capsule or a seamless capsule is preferable and a seamless capsule is more preferable.

In the present invention, the ω3PUFA salt/ester is usually contained in the capsule content. The capsule content may contain general additives to be described later.

The composition of the capsule coating in the soft capsule and the compound preparation of the present invention is not necessarily limited. Exemplary main ingredients include gelatin, carrageenan, pectin, pullulan, sodium alginate, starch, hypromellose, hydroxypropyl cellulose and various known ingredients and gelation is preferable. The gelatin is not limited but known gelatins including acid-treated gelatins, alkali-treated gelatins, amphoteric gelatins and chemically modified gelatins may be used. These gelatins may be used singly or in combination of two or more. Acid-treated gelatins or alkali-treated gelatins are preferable. The gelatins are derived from, for example, cow bones, cow skin, pig bones, pig skin, fish scales and fish skin, and preferably from cow bones, cow skin, pig bones and pig skin although the source is not limited thereto.

Exemplary gelatins include those commonly used in the manufacture of soft capsules, for example, pharmaceutical gelatins (gelatins and purified gelatins) as defined in the Japanese Pharmacopoeia Sixteenth Edition. The gelatins may be used in combination of two or more thereof. In addition, the capsule coating may contain a plasticizer.

Plasticizers that may be preferably used include those commonly used in the manufacture of soft capsules, as exemplified by polyalcohols such as glycerin (e.g., concentrated glycerin), ethylene glycol, polyethylene glycol, propylene glycol and polypropylene glycol; and sugar alcohols such as sorbitol, mannitol and xylitol. The plasticizers may be used in combination of two or more thereof. Of these, glycerin and sorbitol are preferable. It is also preferable to use glycerin in combination with sorbitol. In this case, glycerin and sorbitol are preferably used in a weight ratio of 1:5 to 5:1 and more preferably 1:3 to 3:1.

In the soft capsule and particularly the seamless capsule of the present invention, the capsule coating solution preferably contains the gelatin and the plasticizer so that the weight ratio therebetween may be 10:1 to 1:10 and more preferably 10:1 to 1:1.

The weight ratio between the capsule coating solution and the capsule content is usually 10:1 to 1:10 and preferably 3:1 to 1:10.

In addition, various additives commonly used in the capsule coating, as exemplified by plasticizers such as amino acids, citric acid, glycerin and sorbitol; preservatives; colorants such as dyes and titanium oxide; and organic acids may be optionally added.

The capsule coating composition can be manufactured by dissolving the gelatin, the plasticizer and optionally various additives in water through mixing at room temperature or elevated temperature.

Broadly speaking, the capsule coating can be manufactured by making a film from the capsule coating composition, forming it into a predetermined shape and drying. The moisture content in the dried capsule coating is not limited and is preferably 3 to 20 wt % and most preferably 5 to 15 wt %.

The shaping of the capsule coating and the timing of the material filling vary with the type of the capsule manufactured.

In the soft capsule and the compound preparation of the present invention, the statin stability is improved by adjusting the pH of the capsule coating to a slightly alkaline level. The capsule coating has a pH of, for example, 7.0 to 9.5, preferably 7.0 to 9.0, more preferably 7.0 to 8.0 and most preferably 7.5 to 8.0. The pH of the capsule coating is usually that of the capsule coating solution and may be the measured pH of the capsule coating. The measured pH of the capsule coating is the pH measured when the capsule coating is dissolved in water at a weight ratio of 0.5 to 10.

Various additive ingredients may be further applied to improve the stability of statin and examples thereof include phosphates such as calcium monohydrogen phosphate, sodium monohydrogen phosphate, trisodium phosphate, sodium hydrogen phosphate, calcium hydrogen phosphate, sodium hydrogen phosphate, dipotassium phosphate, potassium dihydrogen phosphate, calcium dihydrogen phosphate and sodium dihydrogen phosphate and hydrates thereof; carbonates such as potassium carbonate, calcium carbonate, potassium hydrogen carbonate, sodium hydrogen carbonate and magnesium carbonate and hydrates thereof; magnesium metasilicate aluminate and other metasilicate aluminate; and magnesium silicate aluminate and other silicate aluminate. A carbonate, a phosphate or a metasilicate aluminate is preferable, a carbonate or a metasilicate aluminate is more preferable and a carbonate is even more preferable. These additives are usually contained in the coating in an amount of 0.2 to 8 wt % and more preferably 0.5 to 5 wt.

In the soft capsule and compound preparation of the present invention, the capsule coating and particularly the gelatin coating are desirably processed with a modification or insolubilization preventing means. More specifically, it is possible to add at least one selected from the group consisting of succinylated gelatin, an organic acid, hydrolyzed gelatin and trehalose to the capsule coating solution, add a water-soluble polymer to the ω3PUFA salt/ester (capsule content) and/or apply a water-soluble polymer to the inner surface of the capsule coating.

The organic acid is not necessarily limited. Examples thereof include tartaric acid, citric acid, amino acids, phosphorylated inositols such as phytin, fumaric acid, succinic acid, lactic acid, malic acid and maleic acid, and tartaric acid is preferred. These organic acids are usually contained in the coating in an amount of 0.2 to 10 wt % and preferably 1.0 to 5 wt %. Succinylated gelatin is usually contained in the coating in an amount of 1 to 40 wt % and more preferably 5 to 20 wt %. Hydrolyzed gelatin is usually contained in the coating in an amount of 1 to 50 wt % and more preferably 5 to 25 wt %. Trehalose is usually contained in the coating in an amount of 1 to 35 wt % and more preferably 4 to 16 wt %. Upon the addition of two or more of the foregoing compounds, the amounts of addition of the respective compounds may also be further reduced to below the preferred ranges.

Water-soluble polymers including general-purpose polymers commonly used in pharmaceutical agents such as HPMC, hydroxypropyl cellulose (hereinafter referred to as "HPC"), methylcellulose (hereinafter referred to as "MC") and polyvinyl pyrrolidone (hereinafter referred to as "PVP") may be used singly or in combination. HPMC, HPC and PVP are preferable in terms of oil resistance and HPMC is particularly preferable. A film can be formed on the inner surface of the capsule coating by suspending any of these water-soluble polymers in the capsule content and encapsulating it. These water-soluble polymers are usually contained in the capsule content in an amount of 0.5 to 20 wt % and preferably 1.0 to 10 wt %.

Addition of at least one selected from the group consisting of succinylated gelatin, an organic acid, hydrolyzed gelatin and trehalose to the capsule coating solution may also be combined with addition of a water-soluble polymer to the ω3PUFA salt/ester (capsule content) and/or application of a water-soluble polymer to the inner surface of the capsule coating. In this case, the amounts of addition of the respective compounds may also be further reduced to below the preferred ranges.

The encapsulation method is not necessarily limited in the present invention and various known methods may be applied, as exemplified by a seamless capsule method through dropping in fluid from a concentric double nozzle and a soft capsule method by means of a rotary process using a rotary soft capsule filling machine.

The dosage and administration period of the ω3PUFA salt/ester and statin that may be used in the compound preparation of the present invention are determined so as to be sufficient for the expression of the intended action and may be adequately increased or decreased depending on the administration route, frequency of daily administration, severity of symptoms, body weight, age, and the like. The single dosage of the ω3PUFA salt/ester and statin may be used for reference and the dosage of one or both of them may be reduced in consideration of the additive or synergistic effect of both the ingredients. In such a case, the effect of reducing the side effects of the respective ingredients is also expected.

When orally administered, the ω3PUFA salt/ester is administered at a dose in terms of EPA-E of 0.1 to 5 g/day, preferably 0.2 to 3 g/day and more preferably 0.4 to 1.8 g/day. The statin is administered at a dose in terms of pravastatin sodium of 0.1 to 100 mg/day, preferably 1 to 80 mg/day and more preferably 2 to 20 mg/day, and at a dose in terms of rosuvastatin calcium of 0.1 to 100 mg/day, preferably 0.5 to 40 mg/day and more preferably 1 to 20 mg/day. The compound preparation of the present invention is administered in a single daily dose or in two or three divided doses but may be optionally divided into several smaller doses for administration. The absorption of the ω3PUFA salt/ester is affected by the diet and therefore the compound preparation is preferably administered during or after meals and more preferably just after meals (within 30 minutes).

The compound preparation of the present invention may further contain a preservative and an antioxidant. Examples of the preservative include ethyl parahydroxybenzoate and propyl parahydroxybenzoate. Examples of the antioxidant include water-soluble antioxidants such as ascorbic acid, erythorbic acid, sodium hydrogen sulfite and sodium pyrosulfite; and oil-soluble antioxidants such as butylated hydroxytoluene, butylated hydroxyanisole, propyl gallate, propyl gallate, a pharmaceutically acceptable quinone, astaxanthin and α-tocopherol, tocopherol acetate and palmitate ascorbate. The water-soluble antioxidants and the oil-soluble antioxidants can be added to the capsule coating solution and the ω3PUFA salt/ester, respectively.

A commonly used suitable carrier or medium, a colorant, a flavor material, optionally a vegetable oil, or further a non-toxic organic solvent or a non-toxic solubilizing agent (for example, glycerin), an emulsifier, a suspending agent (for example, Tween 80, gum arabic solution), an isotonic agent, a pH adjuster, a stabilizer, a flavoring substance, a flavoring agent, a preservative, an antioxidant, an absorption promoter and other additives may be appropriately selected and combined to prepare an adequate compound preparation.

EXAMPLES

The present invention is described below by way of examples. However, the present invention should not be construed as being limited to the following examples.

Example 1

To the mixture obtained by mixing 310.5 g of gelatin (Nippi, Inc.), 33.0 g of sorbitol, 31.5 g of concentrated glycerin, 3.0 g of anhydrous ethanol, 9.6 g of sodium hydrogen carbonate and purified water, was added 0.5 mol/L of sodium hydroxide to adjust the pH, and 9.0 g of pravastatin sodium and purified water were added and dissolved to obtain a coating solution with a total amount of 1500 g and a pH of 8.5 to 9.0. EPA-E was used as the capsule liquid. The coating solution and the capsule liquid were dropped in fluid through a concentric double nozzle to obtain capsules. Then, these capsules were dried to obtain seamless capsules with a diameter of about 4 mm containing EPA-E and pravastatin sodium at a formulation ratio of 90:1. The manufactured seamless capsules were put in an aluminum laminated bag. The bag was purged with nitrogen, hermetically sealed and stored. The formulation of the coating solution is shown in Table 1.

TABLE 1

| | Ingredient | Formulation (wt. %) |
|---|---|---|
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Sodium hydrogen carbonate | 0.64 |
| | 0.5 mol/L aqueous sodium hydroxide solution | q.s. |
| | Purified water | q.s. |
| | Total | 100.00 |

Example 2

To the mixture obtained by mixing 310.5 g of gelatin, 33.0 g of sorbitol, 31.5 g of concentrated glycerin, 3.0 g of anhydrous ethanol, 18.0 g of magnesium metasilicate aluminate, 12.0 g of sodium dihydrogen phosphate dihydrate and purified water, was added 0.5 mol/L of sodium hydroxide to adjust the pH, and 9.0 g of pravastatin sodium and purified water were added and dissolved to obtain a coating solution with a total amount of 1500 g and a pH of 8.5 to 9.0. EPA-E was used as the capsule liquid. Then, seamless capsules were prepared and stored by the same method as in Example 1. The formulation of the coating solution is shown in Table 2.

TABLE 2

| | Ingredient | Formulation (wt. %) |
|---|---|---|
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Magnesium metasilicate aluminate | 1.20 |
| | Sodium dihydrogen phosphate dihydrate | 0.80 |

TABLE 2-continued

| Ingredient | Formulation (wt. %) |
| --- | --- |
| 0.5 mol/L aqueous sodium hydroxide solution | q.s. |
| Purified water | q.s. |
| Total | 100.00 |

Example 3

To the mixture obtained by mixing 310.5 g of gelatin, 33.0 g of sorbitol, 31.5 g of concentrated glycerin, 3.0 g of anhydrous ethanol, 12.0 g of sodium dihydrogen phosphate dihydrate and purified water, was added 0.5 mol/L of sodium hydroxide to adjust the pH, and 9.0 g of pravastatin sodium and purified water were added and dissolved to obtain a coating solution with a total amount of 1500 g and a pH of 8.5 to 9.5. EPA-E was used as the capsule liquid. Then, seamless capsules were prepared and stored by the same method as in Example 1. The formulation of the coating solution is shown in Table 3.

TABLE 3

| | Ingredient | Formulation (wt. %) |
| --- | --- | --- |
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Sodium dihydrogen phosphate dihydrate | 0.80 |
| | 0.5 mol/L aqueous sodium hydroxide solution | q.s. |
| | Purified water | q.s. |
| | Total | 100.00 |

Example 4

To the mixture obtained by mixing 375.0 g of gelatin, 33.0 g of sorbitol, 31.5 g of concentrated glycerin, 3.0 g of anhydrous ethanol, 9.6 g of sodium hydrogen carbonate and purified water, was added 0.5 mol/L of sodium hydroxide to adjust the pH, and purified water was added to obtain a coating solution with a total amount of 1500 g and a pH of 8.5 to 9.0. Separately, 10.0 g of pravastatin sodium was suspended in 900.0 g of EPA-E and the suspension was used as the capsule liquid. Then, seamless capsules were prepared and stored by the same method as in Example 1. The formulation of the coating solution is shown in Table 4.

TABLE 4

| | Ingredient | Formulation (wt. %) |
| --- | --- | --- |
| Coating solution | Gelatin | 25.0 |
| | Sorbitol | 2.20 |
| | Concentrated glycerin | 2.10 |
| | Anhydrous ethanol | 0.20 |
| | Sodium hydrogen carbonate | 0.64 |
| | 0.5 mol/L aqueous sodium hydroxide solution | q.s. |
| | Purified water | q.s. |
| | Total | 100.00 |

Example 5

To the mixture obtained by mixing 414.0 g of gelatin, 44.0 g of sorbitol, 42.0 g of concentrated glycerin, 4.0 g of anhydrous ethanol, 6.4 g of sodium hydrogen carbonate and purified water, was added 0.5 mol/L of sodium hydroxide to adjust the pH, and 12.0 g of pravastatin sodium and purified water were added and dissolved to obtain a coating solution with a total amount of 2000 g and a pH of 7.5 to 8.0. Separately, anhydrous ethanol in an amount corresponding to 1.3 wt % was mixed with EPA-E and the mixture was used as the capsule liquid. Then, seamless capsules were prepared and stored by the same method as in Example 1. The formulation of the coating solution is shown in Table 5.

TABLE 5

| | Ingredient | Formulation (wt. %) |
| --- | --- | --- |
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Sodium hydrogen carbonate | 0.32 |
| | 0.5 mol/L aqueous sodium hydroxide solution | q.s. |
| | Purified water | q.s. |
| | Total | 100.00 |

Example 6

To the mixture obtained by mixing 400.0 g of gelatin, 50.0 g of succinylated gelatin (Nippi, Inc.), 44.0 g of sorbitol, 42.0 g of concentrated glycerin, 4.0 g of anhydrous ethanol, 6.4 g of sodium hydrogen carbonate and purified water, was added 0.5 mol/L of sodium hydroxide to adjust the pH, and 12.0 g of pravastatin sodium and purified water were added and dissolved to obtain a coating solution with a total amount of 2000 g and a pH of 7.5 to 8.0. Separately, anhydrous ethanol in an amount corresponding to 1.3 wt % was mixed with EPA-E and the mixture was used as the capsule liquid. Then, seamless capsules were prepared and stored by the same method as in Example 1. The formulation of the coating solution is shown in Table 6.

TABLE 6

| | Ingredient | Formulation (wt. %) |
| --- | --- | --- |
| Coating solution | Pravastatin sodium | 0.60 |
| | Gelatin | 20.00 |
| | Succinylated gelatin | 2.50 |
| | Sorbitol | 2.20 |
| | Concentrated glycerin | 2.10 |
| | Anhydrous ethanol | 0.20 |
| | Sodium hydrogen carbonate | 0.32 |
| | 0.5 mol/L aqueous sodium hydroxide solution | q.s. |
| | Purified water | q.s. |
| | Total | 100.00 |

Example 7

To the mixture obtained by mixing 400.0 g of gelatin, 50.0 g of succinylated gelatin, 44.0 g of sorbitol, 42.0 g of concentrated glycerin, 4.0 g of anhydrous ethanol, 6.4 g of sodium hydrogen carbonate and purified water, was added 0.5 mol/L of sodium hydroxide to adjust the pH, and 12.0 g of pravastatin sodium and purified water were added and dissolved to obtain a coating solution with a total amount of 2000 g and a pH of 8.0 to 8.5. Separately, anhydrous ethanol in an amount corresponding to 1.3 wt % was mixed with EPA-E and the mixture was used as the capsule liquid. Then, seamless capsules were prepared and stored by the same method as in Example 1. The formulation of the coating solution is shown in Table 7.

TABLE 7

| | Ingredient | Formulation (wt. %) |
|---|---|---|
| Coating solution | Pravastatin sodium | 0.60 |
| | Gelatin | 20.00 |
| | Succinylated gelatin | 2.50 |
| | Sorbitol | 2.20 |
| | Concentrated glycerin | 2.10 |
| | Anhydrous ethanol | 0.20 |
| | Sodium hydrogen carbonate | 0.32 |
| | 0.5 mol/L aqueous sodium hydroxide | q.s. |
| | Purified water | q.s. |
| | Total | 100.00 |

Example 8

To the mixture obtained by mixing 414.0 g of gelatin, 44.0 g of sorbitol, 42.0 g of concentrated glycerin, 4.0 g of anhydrous ethanol, 6.4 g of sodium hydrogen carbonate and purified water, were added 12.0 g of tartaric acid and sodium hydroxide to adjust the pH, and 12.0 g of pravastatin sodium and purified water were added and dissolved to obtain a coating solution with a total amount of 2000 g and a pH of 7.5 to 8.0. Separately, anhydrous ethanol in an amount corresponding to 1.3 wt % was mixed with EPA-E and the mixture was used as the capsule liquid. Then, seamless capsules were prepared and stored by the same method as in Example 1. The formulation of the coating solution is shown in Table 8.

TABLE 8

| | Ingredient | Formulation (wt. %) |
|---|---|---|
| Coating solution | Pravastatin sodium | 0.60 |
| | Gelatin | 20.70 |
| | Tartaric acid | 0.60 |
| | Sorbitol | 2.20 |
| | Concentrated glycerin | 2.10 |
| | Anhydrous ethanol | 0.20 |
| | Sodium hydrogen carbonate | 0.32 |
| | Sodium hydroxide | q.s. |
| | Purified water | q.s. |
| | Total | 100.00 |

Example 9

To the mixture obtained by mixing 400.0 g of gelatin, 50.0 g of succinylated gelatin, 44.0 g of sorbitol, 42.0 g of concentrated glycerin, 4.0 g of anhydrous ethanol, 6.4 g of sodium hydrogen carbonate and purified water, were added 12.0 g of tartaric acid and sodium hydroxide to adjust the pH, and 12.0 g of pravastatin sodium and purified water were added and dissolved to obtain a coating solution with a total amount of 2000 g and a pH of 7.5 to 8.0. Separately, anhydrous ethanol in an amount corresponding to 1.3 wt % was mixed with EPA-E and the mixture was used as the capsule liquid. Then, seamless capsules were prepared and stored by the same method as in Example 1. The formulation of the coating solution is shown in Table 9.

TABLE 9

| | Ingredient | Formulation (wt. %) |
|---|---|---|
| Coating solution | Pravastatin sodium | 0.60 |
| | Gelatin | 20.00 |
| | Succinylated gelatin | 2.50 |
| | Tartaric acid | 0.60 |
| | Sorbitol | 2.20 |
| | Concentrated glycerin | 2.10 |
| | Anhydrous ethanol | 0.20 |
| | Sodium hydrogen carbonate | 0.32 |
| | Sodium hydroxide | q.s. |
| | Purified water | q.s. |
| | Total | 100.00 |

Example 10

To the mixture obtained by mixing 414.0 g of gelatin, 44.0 g of sorbitol, 42.0 g of concentrated glycerin, 4.0 g of anhydrous ethanol, 6.4 g of sodium hydrogen carbonate and purified water, was added 0.5 mol/L of sodium hydroxide to adjust the pH, and 12.0 g of pravastatin sodium and purified water were added and dissolved to obtain a coating solution with a total amount of 2000 g and a pH of 7.5 to 8.0. Separately, 30 g of HPMC (TC-5E available from Shin-Etsu Chemical Co., Ltd.) was dispersed in 970 g of EPA-E and the dispersion was used as the capsule liquid. Then, the method of Example 1 was repeated to prepare two-layered seamless capsules each having an HPMC layer formed between the gelatin coating and the capsule liquid. The seamless capsules were put in an aluminum laminated bag. The bag was purged with nitrogen, hermetically sealed and stored. The formulation of the coating solution is shown in Table 10.

TABLE 10

| | Ingredient | Formulation (wt. %) |
|---|---|---|
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Sodium hydrogen carbonate | 0.32 |
| | 0.5 mol/L aqueous sodium hydroxide solution | q.s. |
| | Purified water | q.s. |
| | Total | 100.00 |

Example 11

To the mixture obtained by mixing 69.0 kg of gelatin, 30.3 kg of concentrated glycerin, 2.07 kg of sodium hydrogen carbonate and purified water, were added sodium hydroxide and purified water to adjust the pH to thereby obtain a coating solution with a total amount of 160 kg and a pH of 8.5 to 9.0. Separately, 10.0 g of pravastatin sodium was suspended in 900.0 g of EPA-E and the suspension was used as the capsule liquid. The coating solution was used to prepare a gelatin sheet. Capsules were punched out of the sheet using dies as the capsule liquid was filled thereinto to obtain soft capsules by a rotary process. The manufactured soft capsules were put in an aluminum laminated bag and the bag was hermetically sealed. The formulation of the coating solution is shown in Table 11.

TABLE 11

| | Ingredient | Formulation (wt. %) |
|---|---|---|
| Coating solution | Gelatin | 100.0 |
| | Concentrated glycerin | 44.0 |
| | Sodium hydrogen carbonate | 3.0 |
| | Sodium hydroxide | q.s. |
| | Purified water | q.s. |
| | Total | 232.0 |

Example 12

To the mixture obtained by mixing 33.2 kg of gelatin, 33.2 kg of succinylated gelatin, 19.9 kg of concentrated glycerin, 1.99 kg of sodium hydrogen carbonate and purified water, were added sodium hydroxide and purified water to adjust the pH to thereby obtain a coating solution with a total amount of 160 kg and a pH of 8.5 to 9.0. Separately, 10.0 g of pravastatin sodium was suspended in 900.0 g of EPA-E and the suspension was used as the capsule liquid. Then, soft capsules were prepared and stored by the same method as in Example 11. The formulation of the coating solution is shown in Table 12.

TABLE 12

| | Ingredient | Formulation (wt. %) |
|---|---|---|
| Coating solution | Gelatin | 50.0 |
| | Succinylated gelatin | 50.0 |
| | Concentrated glycerin | 30.0 |
| | Sodium hydrogen carbonate | 3.0 |
| | Sodium hydroxide | q.s. |
| | Purified water | q.s. |
| | Total | 241.0 |

Example 13

To the mixture obtained by mixing 33.2 kg of gelatin, 33.2 kg of succinylated gelatin, 19.9 kg of concentrated glycerin, 1.99 kg of sodium hydrogen carbonate, 3.85 kg of magnesium metasilicate aluminate and purified water, were added sodium hydroxide and purified water to adjust the pH to thereby obtain a coating solution with a total amount of 160 kg and a pH of 8.5 to 9.0. Separately, 10.0 g of pravastatin sodium was suspended in 900.0 g of EPA-E and the suspension was used as the capsule liquid. Then, soft capsules were prepared and stored by the same method as in Example 11. The formulation of the coating solution is shown in Table 13.

TABLE 13

| | Ingredient | Formulation (wt. %) |
|---|---|---|
| Coating solution | Gelatin | 50.0 |
| | Succinylated gelatin | 50.0 |
| | Concentrated glycerin | 30.0 |
| | Sodium hydrogen carbonate | 3.0 |
| | Magnesium metasilicate aluminate | 5.8 |

TABLE 13-continued

| Ingredient | Formulation (wt. %) |
|---|---|
| Sodium hydroxide | q.s. |
| Purified water | q.s. |
| Total | 241.0 |

Example 14

To the mixture obtained by mixing 33.2 kg of gelatin, 33.2 kg of succinylated gelatin, 19.9 kg of concentrated glycerin, 1.99 kg of sodium hydrogen carbonate and purified water, are added sodium hydroxide and purified water to adjust the pH to thereby obtain a coating solution with a total amount of 160 kg and a pH of 7.5 to 8.5. Separately, 10.0 g of pravastatin sodium is suspended in 900.0 g of EPA-E and the suspension is used as the capsule liquid. Then, soft capsules are prepared and stored by the same method as in Example 11. The formulation of the coating solution is shown in Table 14.

TABLE 14

| | Ingredient | Formulation (wt. %) |
|---|---|---|
| Coating solution | Gelatin | 50.0 |
| | Succinylated gelatin | 50.0 |
| | Concentrated glycerin | 30.0 |
| | Sodium hydrogen carbonate | 3.0 |
| | Sodium hydroxide | q.s. |
| | Purified water | q.s. |
| | Total | 241.0 |

Example 15

To the mixture obtained by mixing 310.5 g of gelatin, 33.0 g of sorbitol, 31.5 g of concentrated glycerin, 3.0 g of anhydrous ethanol and purified water, was added 0.5 mol/L of sodium hydroxide to adjust the pH, and 9.0 g of pravastatin sodium and purified water were added and dissolved to obtain a coating solution with a total amount of 1500 g and a pH of 8.5 to 9.0. EPA-E was used as the capsule liquid. Then, seamless capsules were prepared and stored by the same method as in Example 1. The formulation of the coating solution is shown in Table 15.

TABLE 15

| | Ingredient | Formulation (wt. %) |
|---|---|---|
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | 0.5 mol/L aqueous sodium hydroxide solution | q.s. |
| | Purified water | q.s. |
| | Total | 100.00 |

Examples 16-1 to 16-15

The methods described in Examples 1 to 15 are repeated except that pravastatin sodium is replaced by rosuvastatin calcium and EPA-E and the rosuvastatin calcium are used at a formulation ratio of 720:1, thereby obtaining seamless capsules with a diameter of about 4 mm or rotary soft capsules. Then, the capsules are stored by the same method as in Example 1. The formulation of each coating solution is shown in Table 16.

TABLE 16

| | Ingredient | Example 16-1 | 16-2 | 16-3 | 16-4 | 16-5 |
|---|---|---|---|---|---|---|
| | | Formulation (wt. %) | | | | |
| Coating solution | Rosuvastatin calcium | 0.075 | 0.075 | 0.075 | — | 0.075 |
| | Gelatin | 20.70 | 20.70 | 20.70 | 25.00 | 20.70 |
| | Succinylated gelatin | — | — | — | — | — |
| | Tartaric acid | — | — | — | — | — |
| | Sorbitol | 2.20 | 2.20 | 2.20 | 2.20 | 2.20 |
| | Concentrated glycerin | 2.10 | 2.10 | 2.10 | 2.10 | 2.10 |
| | Anhydrous ethanol | 0.20 | 0.20 | 0.20 | 0.20 | 0.20 |
| | Sodium hydrogen carbonate | 0.64 | — | — | 0.64 | 0.32 |
| | Magnesium metasilicate aluminate | — | 1.20 | — | — | — |
| | Sodium dihydrogen phosphate dihydrate | — | 0.80 | 0.80 | — | — |
| | 0.5 mol/L aqueous sodium hydroxide solution | q.s. | q.s. | q.s. | q.s. | q.s. |
| | Purified water | q.s. | q.s. | q.s. | q.s. | q.s. |
| | Total | 100.00 | 100.00 | 100.00 | 100.00 | 100.00 |
| | pH | 8.5-9.0 | 8.5-9.0 | 8.5-9.5 | 8.5-9.0 | 7.5-8.0 |

| | Ingredient | Example 16-6 | 16-7 | 16-8 | 16-9 | 16-10 |
|---|---|---|---|---|---|---|
| | | Formulation (wt. %) | | | | |
| Coating solution | Rosuvastatin calcium | 0.075 | 0.075 | 0.075 | 0.075 | 0.075 |
| | Gelatin | 20.00 | 20.00 | 20.70 | 20.00 | 20.70 |
| | Succinylated gelatin | 2.50 | 2.50 | — | 2.50 | — |
| | Tartaric acid | — | — | 0.60 | 0.60 | — |
| | Sorbitol | 2.20 | 2.20 | 2.20 | 2.20 | 2.20 |
| | Concentrated glycerin | 2.10 | 2.10 | 2.10 | 2.10 | 2.10 |
| | Anhydrous ethanol | 0.20 | 0.20 | 0.20 | 0.20 | 0.20 |
| | Sodium hydrogen carbonate | 0.32 | 0.32 | 0.32 | 0.32 | 0.32 |
| | Magnesium metasilicate aluminate | — | — | — | — | — |
| | Sodium dihydrogen phosphate dihydrate | — | — | — | — | — |
| | 0.5 mol/L aqueous sodium hydroxide solution | q.s. | q.s. | q.s. | q.s. | q.s. |
| | Purified water | q.s. | q.s. | q.s. | q.s. | q.s. |
| | Total | 100.00 | 100.00 | 100.00 | 100.00 | 100.00 |
| | pH | 7.5-8.0 | 8.0-8.5 | 7.5-8.0 | 7.5-8.0 | 7.5-8.0 |

| | Ingredient | Example 16-11 | 16-12 | 16-13 | 16-14 | 16-15 |
|---|---|---|---|---|---|---|
| | | Formulation (wt. %) | | | | |
| Coating solution | Rosuvastatin calcium | — | — | — | — | 0.075 |
| | Gelatin | 100.00 | 50.00 | 50.00 | 50.00 | 20.70 |
| | Succinylated gelatin | — | 50.00 | 50.00 | 50.00 | — |
| | Tartaric acid | — | — | — | — | — |
| | Sorbitol | — | — | — | — | 2.20 |
| | Concentrated glycerin | 44.00 | 30.00 | 30.00 | 30.00 | 2.10 |
| | Anhydrous ethanol | — | — | — | — | 0.20 |
| | Sodium hydrogen carbonate | 3.00 | 3.00 | 3.00 | 3.00 | — |
| | Magnesium metasilicate aluminate | — | — | 5.80 | — | — |
| | Sodium dihydrogen phosphate dihydrate | — | — | — | — | — |
| | 0.5 mol/L aqueous sodium hydroxide solution | q.s. | q.s. | q.s. | q.s. | q.s. |
| | Purified water | q.s. | q.s. | q.s. | q.s. | q.s. |
| | Total | 232.00 | 241.00 | 241.00 | 241.00 | 100.00 |
| | pH | 8.5-9.0 | 8.5-9.0 | 8.5-9.0 | 7.5-8.5 | 8.5-9.0 |

Comparative Example 1

To the mixture obtained by mixing 372.6 g of gelatin, 39.6 g of sorbitol, 37.8 g of concentrated glycerin, 3.6 g of anhydrous ethanol and purified water, 10.8 g of pravastatin sodium and purified water were added and dissolved to obtain a coating solution with a total amount of 1800 g and a pH of up to 7.0. Separately, anhydrous ethanol in an amount corresponding to 1.5 wt % was mixed with EPA-E and the mixture was used as the capsule liquid. Then, seamless capsules were prepared and stored by the same method as in Example 1. The formulation of the coating solution is shown in Table 17.

TABLE 17

| | Ingredient | Formulation (wt. %) |
|---|---|---|
| Coating solution | Pravastatin sodium | 0.60 |
| | Gelatin | 20.70 |
| | Sorbitol | 2.20 |
| | Concentrated glycerin | 2.10 |
| | Anhydrous ethanol | 0.20 |
| | Purified water | q.s. |
| | Total | 100.00 |

Comparative Example 2

The mixture obtained by mixing 77.29 kg of gelatin, 34.16 kg of concentrated glycerin and purified water had a total amount of 180 kg and a pH of up to 7.0 and was used as the coating solution. Separately, 10.0 g of pravastatin sodium was suspended in 900.0 g of EPA-E and the suspension was used as the capsule liquid. Then, soft capsules were prepared and stored by the same method as in Example 11. The formulation of the coating solution is shown in Table 18.

TABLE 18

| | Ingredient | Formulation (wt. %) |
|---|---|---|
| Coating solution | Gelatin | 100.0 |
| | Concentrated glycerin | 44.2 |
| | Purified water | q.s. |
| | Total | 232.9 |

Test Example 1

Stabilization of Pravastatin Sodium (Seamless Capsules)

The respective seamless capsules in Examples 1 to 9 and 15 and Comparative Example 1 were kept at 40° C. or 50° C. to perform an aging test. Pravastatin sodium analogs were extracted from the seamless capsules at the beginning, after the storage at 40° C. and a relative humidity of 75% (indicated as 75% RH in the table) for 4 weeks (indicated as 4W in the table) or after the storage at 50° C. for 10 days, and analyzed by high-performance liquid chromatography (abbreviated as "HPLC") according to a conventional process. The total amounts of the seamless capsule analogs are shown in Table 19.

TABLE 19

| | Beginning | 40° C. 75% RH 4 W | 50° C. 10 days |
|---|---|---|---|
| Example 1 | 0.14% | 0.13% | — |
| Example 2 | 0.19% | 0.17% | — |
| Example 3 | 0.20% | 0.50% | — |
| Example 4 | 0.21% | 0.19% | — |
| Example 5 | 0.19% | — | 0.21% |
| Example 6 | 0.20% | — | 0.19% |
| Example 7 | 0.25% | — | 0.25% |
| Example 8 | 0.20% | — | 0.19% |
| Example 9 | 0.17% | — | 0.19% |
| Example 15 | 0.27% | 1.00% | — |
| Comparative Example 1 | 1.08% | 8.75% | — |

The total amount of the pravastatin sodium analogs in Comparative Example 1 was more than 1% at the beginning and increased to 8% or more after the high-temperature accelerated test, whereas that in each of Examples 1 to 9 was up to 0.50% not only at the beginning but also after the high-temperature accelerated test. The total amount of the pravastatin sodium analogs in Example 15 was up to 0.50% at the beginning and 1% after the high-temperature accelerated test. In other words, the seamless capsules of the present invention exhibited a statin-stabilizing effect during the manufacture and storage thereof. In particular, Examples 3 to 9 in which a carbonate, a phosphate or a metasilicate aluminate was added exhibited a particularly high statin-stabilizing effect during the storage thereof.

Test Example 2

Suppression of Modification of Gelatin

Coating A, Coating B

Each of the coating solutions whose formulation is shown in Table 20 was prepared, applied to a petri dish and dried to prepare a gelatin coating. The thus prepared gelatin coating was immersed in EPA-E, purged with nitrogen, hermetically sealed and stored at 60° C. for 10 days. Then, the appearance of the coating was evaluated.

Coating C, Coating D

Each of the coating solutions whose formulation is shown in Table 20 was prepared, formed into a bar shape using a syringe and dried to prepare a bar-shaped gelatin coating with a weight of about 0.3 g. The thus prepared gelatin coating was immersed in EPA-E, purged with nitrogen, hermetically sealed and stored at 50° C. for 10 days. The stored coating was dissolved in 900 mL of hot water at 37° C. The solution was filtered through a filter with a pore size of 1 μm and the insolubilization ratio (%) was calculated by the following formula based on the dry weight of the insoluble substance on the filter.

Insolubilization ratio (%)={dry weight (mg) of insoluble substance/weight (mg) of coating used in test}×100

TABLE 20

| | Ingredient | Coating A | Coating B | Coating C | Coating D |
|---|---|---|---|---|---|
| Coating solution | Pravastatin sodium | 0.60 | 0.60 | 0.60 | 0.60 |
| | Gelatin | 20.00 | 20.70 | 20.74 | 20.71 |
| | Succinylated gelatin | 2.50 | — | — | — |
| | Hydrolyzed gelatin powder | — | — | 3.21 | — |
| | Tartaric acid | — | 1.20 | — | — |
| | Sorbitol | 2.20 | 2.20 | 2.20 | — |
| | Trehalose | — | — | — | 2.20 |
| | Concentrated glycerin | 2.10 | 2.10 | 2.10 | 2.10 |
| | Anhydrous ethanol | 0.20 | 0.20 | 0.20 | 0.20 |
| | Sodium hydrogen carbonate | 0.32 | 0.32 | 0.32 | 0.32 |
| | 0.5 mol/L aqueous sodium hydroxide solution | q.s. | q.s. | q.s. | q.s. |
| | Purified water | q.s. | q.s. | q.s. | q.s. |
| | Total | 100.00 | 100.00 | 100.00 | 100.00 |

TABLE 20-continued

| Ingredient | Coating A | Coating B | Coating C | Coating D |
|---|---|---|---|---|
| pH | 7.5-8.0 | 7.5-8.0 | 7.5-8.0 | 7.5-8.0 |
| Evaluation result of coating appearance (storage at 60° C. for 10 days) | good | good | — | — |
| Evaluation result of insolubilization ratio (storage at 50° C. for 10 days) | — | — | good | good |

Evaluation of the coating appearance: good: no change from the start of the test; poor: thin-film formation
Evaluation of the insolubilization ratio: good: less than 0.3%; poor: 0.30 or more In the coatings A and E in which succinylated gelatin and tartaric acid were added, respectively, there was no change in the coating appearance even after the storage at 60° C. for 10 days. In the coatings C and D in which hydrolyzed gelatin powder and trehalose were added, respectively, the insolubilization ratio was less than 0.3% even after the storage at 50° C. for 10 days. That is, addition of succinylated gelatin, tartaric acid, hydrolyzed gelatin powder or trehalose to the coating of the soft capsule of the present invention was effective in suppressing the modification or insolubilization of the coating during the storage.

Test Example 3

Stabilization of Pravastatin Sodium (Soft Capsules Obtained by a Rotary Process

The respective soft capsules in Examples 11 to 13 and Comparative Example 2 were kept at 40° C. to perform an aging test. Pravastatin sodium analogs were extracted from the soft capsules at the beginning and after the storage at 40° C. and a relative humidity of 75% for 2 weeks or 4 weeks, and analyzed by HPLC according to a conventional process. The total amounts of the analogs of the soft capsules are shown in Table 21.

TABLE 21

| | Beginning | 40° C. 75% RH 2 W | 40° C. 4 W |
|---|---|---|---|
| Example 11 | 0.16% | — | 0.21% |
| Example 12 | 0.16% | — | 0.58% |
| Example 13 | 0.19% | — | 0.67% |
| Comparative Example 2 | 1.98% | 12.10% | — |

The total amount of the pravastatin sodium analogs in Comparative Example 2 was more than 1% at the beginning and increased to 12% or more after the storage at 40° C. for 2 weeks, whereas that in each of Examples 11 to 13 was up to 0.7% not only at the beginning but also after the high-temperature accelerated test. In other words, the soft capsules of the present invention exhibited a statin-stabilizing effect during the manufacture and storage thereof.

The invention claimed is:

1. A compound preparation comprising:
   at least one member selected from the group consisting of ω3 polyunsaturated fatty acids and pharmaceutically acceptable salts and esters thereof, which is contained in a capsule content: and
   a capsule coating with a pH adjusted to 7.0 to 9.5
      wherein said capsule coating comprises the following components a), b), and c):
         a) at least one member selected from the group consisting of water-soluble statin compounds,
         b) a gelatin, and
         c) at least one member selected from the group consisting of a carbonate, metasilicate aluminate, and a phosphate.

2. The compound preparation according to claim 1, wherein the component c) is at least one selected from the group consisting of a carbonate and magnesium metasilicate aluminate.

3. The compound preparation according to claim 1, wherein the capsule coating contains at least one member selected from the group consisting of succinylated gelatin, an organic acid, hydrolyzed gelatin and trehalose.

4. The compound preparation according to claim 1, wherein the water-soluble statin compounds comprise at least one member selected from the group consisting of pravastatin and rosuvastatin, and salts and hydrates thereof.

5. The compound preparation according to claim 3, wherein the organic acid is at least one member selected from the group consisting of tartaric acid, citric acid, amino acids, phosphorylated inositols, thmaric acid, succinic acid, lactic acid, malic acid and maleic acid.

6. The compound preparation according to claim 1, wherein the total amount of pravastatin sodium analogs in the compound preparation is up to 0.7% when stored at 40° C., a relative humidity of 75%, and for 4 weeks.

7. The compound preparation according to claim 1, wherein the total amount of pravastatin sodium analogs in the compound preparation is up to 0.5% when stored at 50° C., a relative humidity of 75%, and for 10 days.

8. A compound preparation comprises at least one member selected from the group consisting of ω3 polyunsaturated fatty acids and pharmaceutically acceptable salts and esters thereof which is contained in a capsule content and a capsule coating with a pH adjusted to 7.0 to 9.5 ,
   wherein said capsule coating comprises:
      a) 0.01 to 20 wt % of at least one member selected from the group consisting of water-soluble statin compounds, based on the total amount of the compound preparation,
      b) a gelatin, and
      c) 0.2 to 8 wt % of at least one member selected from the group consisting of a carbonate, metasilicate aluminate, and a phosphate, based on the total amount of the compound preparation.

9. The compound preparation according to claim 4, wherein the water-soluble statin compound is pravastatin sodium or rosuvastatin calcium.

* * * * *